United States Patent [19]

Fenne et al.

[11] 4,142,419

[45] Mar. 6, 1979

[54] SENSING DEVICE FOR LIQUIDS

[75] Inventors: Ivor Fenne, Greenford; Paul Lakra, Wembley, both of England

[73] Assignee: Lucas Industries Limited, Birmingham, England

[21] Appl. No.: 845,368

[22] Filed: Oct. 25, 1977

[30] Foreign Application Priority Data

Nov. 6, 1976 [GB] United Kingdom ............... 46270/76

[51] Int. Cl.² .............................................. G01N 9/12
[52] U.S. Cl. ....................................... 73/440; 73/447; 73/453
[58] Field of Search ................ 73/440, 451, 452, 453, 73/454, 291, 308, 311, 313, 447; 137/91

[56] References Cited

U.S. PATENT DOCUMENTS

| | | | |
|---|---|---|---|
| 2,333,406 | 11/1943 | Ballard | 73/313 |
| 2,416,808 | 3/1947 | Weiss | 73/452 |
| 2,767,580 | 10/1956 | Bevins et al. | 73/440 |
| 3,333,469 | 8/1967 | Godfrey | 73/308 |
| 3,952,761 | 4/1976 | Friedland | 73/452 |

Primary Examiner—Stephen A. Kreitman

[57] ABSTRACT

A device for indicating changes in the specific gravity of a liquid comprises first and second floats adapted to float on the surface of the liquid, the float having different shapes and/or densities so that the depth of the floats in the liquid varies in accordance with the specific gravity of the liquid and means for producing an electrical signal dependent upon the depth to which the floats are immersed relative to one another.

1 Claim, 1 Drawing Figure

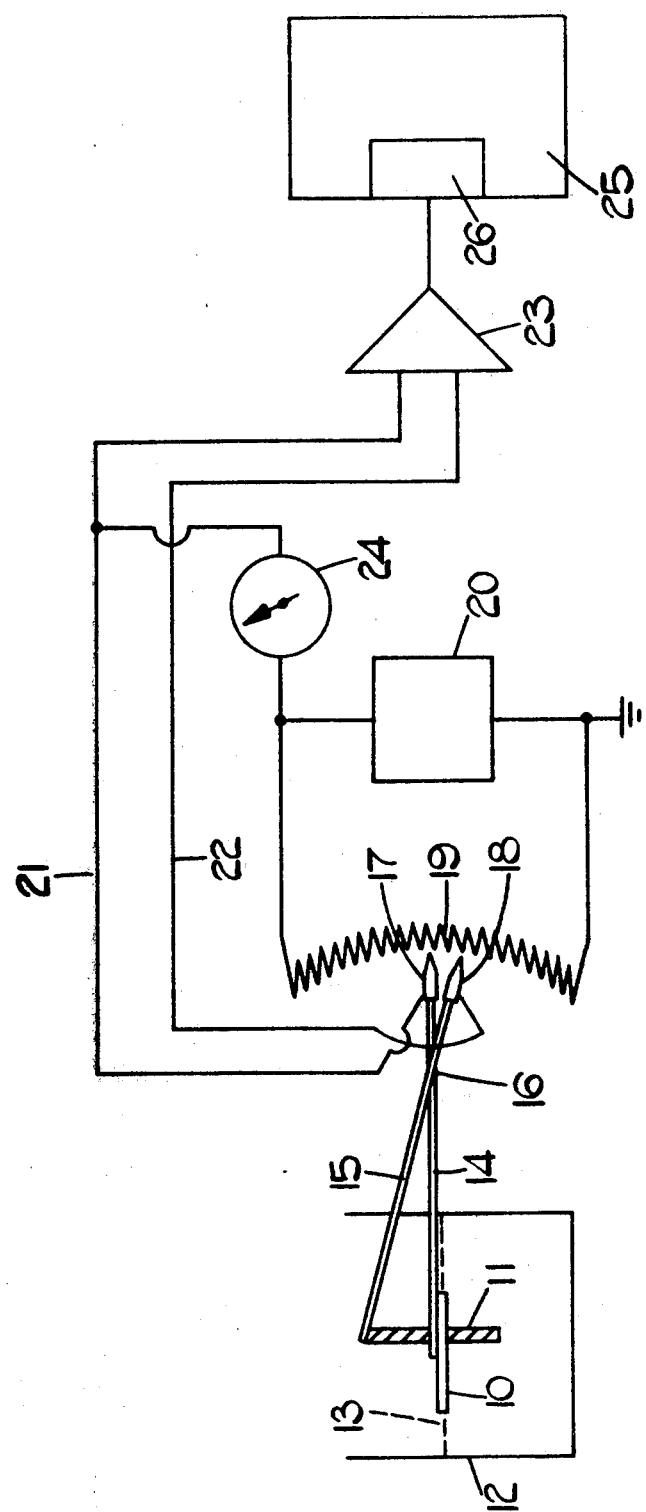

SENSING DEVICE FOR LIQUIDS

This invention relates to a device for indicating changes in the specific gravity of a liquid, where particularly liquid fuel for internal combustion engines.

According to the present invention, there is provided a device for indicating changes in the specific gravity of a liquid comprising first and second floats adapted to float on the surface of said liquid, the shapes and/or densities of said floats being so arranged that the depths to which said floats are immersed in said liquid relative to one another change in response to changes in said specific gravity, and means for producing an electrical signal dependent upon the depths to which said floats are immersed relative to one another.

Preferably, said means for producing an electrical signal includes electrical means for producing a first voltage dependent upon the height of a predetermined point on said first float above or below a given level and a second voltage dependent upon the height of a predetermined point on said second float above or below said given level said electrical signal being provided by the difference between said first and second voltages.

More preferably, said means for producing an electrical signal further includes a differential amplifier which receives said first and second voltages as inputs and produces said electrical signal as an output.

Conveniently, said electrical means comprises a voltage divider including a resistor and a pair of wipers slidable therealong, each wiper being connected to said predetermined point on a respective one of said floats such that a change in height of said predetermined point in use causes the associated wiper to slide along said resistor.

Also according to the present invention, there is provided a fuel system for an internal combustion engine, a fuel tank and fuel adjusting means for adjusting the maximum amount of fuel supplied to said engine, a device for indicating changes in the specific gravity of said fuel, said device comprising first and second floats disposed in said fuel tank and floating on the surface of the fuel container therein, the shapes and/or densities of said floats being so arranged that the depths to which said floats are immersed in said fuel relative to one another changes in response to changes in specific gravity of said fuel, and means for producing an electrical signal dependent upon the depths to which said floats are immersed relative to one another, said electrical signal being used to control said fuel adjusting means.

An embodiment of the present invention will now be described by way of example, with reference to the accompanying drawing, which is a schematic illustration of a device according to the present invention adapted for use in indicating changes in the specific gravity of liquid fuel for an engine.

Referring to the drawing, the device comprises a pair of floats 10 and 11 which are disposed in a fuel tank 12 of a motor vehicle (not shown) so as to float on the surface of fuel contained therein. The surface of the fuel in the tank 12 is indicated in broken line at 13. The floats 10 and 11 are of different shapes for a purpose to be explained later. Each float 10, 11 has connected thereto one end of a respective rod 14, 15, the rods 14 and 15 being commonly pivotally mounted relative to the tank 12 by means of a pivot 16. The ends of the rods 14 and 15 remote from the floats 10 and 11 are provided with electrically conductive wipers 17 and 18, respectively.

The wipers 17 and 18 form part of a voltage divider, which also includes a resistor 19 across which a voltage source 20 is connected. The wipers 17 and 18 engage the resistor 19 and are slidable therealong so that the voltage appearing at each wiper 17, 18 varies according to the latter's position on the resistor 19. Electrical leads 21 and 22 respectively connect the wipers 17 and 18 to respective inputs of a differential amplifier 23, which is arranged to produce as an output, a signal dependent upon the difference between the voltages at its inputs. A voltmeter 24 is connected between the lead 21 and the higher potential end of the resistor 19.

The voltage appearing at each wiper 17, 18 depends on the height above a given level (for example, the floor of the tank 12) of the point of connection between the respective rod 14, 15 and the respective float 10, 11. This height in turn depends on the level of fuel in the tank 12 and the depth to which the respective float 10, 11 is immersed in the fuel.

The depth to which either float 10 or 11 is immersed depends on the specific gravity of the fuel. By making the floats 10 and 11 of different shapes, a change in the specific gravity of the fuel will cause a change in the relative depths to which the floats 10 and 11 are immersed, and therefore a change in the spacing between the points of connection of the rods 14 and 15 to the floats 10 and 11. This in turn will cause a change in the spacing of wipers 17 and 18 and therefore a change in the voltage difference therebetween. The voltages appearing at the wipers 17 and 18 are transmitted to the inputs of the differential amplifier 23 via leads 21 and 22, and the amplifier 23 produces an output dependent upon the difference between these voltages. Thus, a change in the specific gravity of the float in tank 12 will cause a change in the output of amplifier 23.

The output of amplifier 23 is used to control the supply of fuel to an engine (not shown), which is preferably a diesel engine. Fuel is supplied to the engine by means of a supply pump 25 which is provided with means 26 for adjusting its maximum fuel setting. To obtain efficient operation of the engine the maximum fuel setting must be altered when the specific gravity of the fuel and therefore the heating volume of the fuel, being supplied thereto varies.

The output from the amplifier 23 can be used as shown to control the adjusting means of the supply pump directly. Alternatively, for supply pumps in which the adjusting means operates to vary the amount of fuel supplied by the pump for which purpose an actuator controlled by an electronic circuit is provided, the output of amplifier 23 can be fed directly into the electronic control circuit.

As the level of fuel in the tank 12 falls, the relative depths to which the floats 10 and 11 are immersed remains the same (provided, of course, that the specific gravity of the fuel does not change). The resistance of resistor 19 is constant along its length, and therefore the voltage difference between the wipers 17 and 18, and hence the output of amplifier 23, does not change as the fuel level falls.

On the other hand, as the level of fuel in the tank 12 falls, the float 10 and 11 fall also, thereby causing the wipers 17 and 18 to move upwardly along the resistor 19 towards the higher potential end thereof. The voltage difference between each of the wipers 17 and 18 and the higher potential end of resistor 19 thus decreases as the fuel level falls, and thus this voltage difference can be used to give an indication of the amount of fuel remaining in the tank 12, as in a conventional fuel gauge. The voltmeter 24 is provided for this very purpose and measures the voltage difference between the wiper 17 and the higher potential end of resistor 19.

As described above, the device includes two floats of different shapes. Alternatively or additionally, the same effect can be achieved by using two floats of different densities.

We claim:

1. A device for indicating changes in the specific gravity of a liquid, comprising first and second floats adapted to float on the surface of said liquid, the shapes and/or densities of said floats being so arranged that the depths to which said floats are immersed in said liquid relative to one another change in response to changes in said specific gravity, means for producing an electrical signal dependent upon the depths to which said floats are immersed relative to one another, said means comprising electrical means for producing a first voltage dependent upon the height of a predetermined point on said first float relative to a given leval and a second voltage dependent upon the height of a predetermined point on said second float relative to said given level, said electrical signal being provided by the differences between said first and second voltages, a differential amplifier receiving said first and second voltages as imputs and providing said electrical signal, said electrical means comprising a voltage divider including a resistor and a pair of wipers slidable therealong, each wiper being connected to said predetermined point on a respective one of said floats such that a change in height of said predetermined point in use causes the associate wiper to slide along said resistor, and indicating means connected between one of said slides and one end of said resistor for providing an indication of the liquid level in said tank.

* * * * *